US00PP09691P

United States Patent [19]

Leue

[11] Patent Number: Plant 9,691

[45] Date of Patent: Nov. 12, 1996

[54] IMPATIENS PLANT NAMED 'SALMON SUNRISE'

[75] Inventor: Ellen F. Leue, West Chicago, Ill.

[73] Assignee: Geo. J. Ball, Inc., West Chicago, Ill.

[21] Appl. No.: 445,373

[22] Filed: May 19, 1995

[51] Int. Cl.[6] ..... A01H 5/00

[52] U.S. Cl. ..... Plt./87.6

[58] Field of Search ..... Plt./87.6

*Primary Examiner*—Howard J. Locker

*Attorney, Agent, or Firm*—Burns, Doane, Swecker & Mathis, L.L.P.

[57] ABSTRACT

A new and distinct cultivar of Impatiens plant, botanically known as *Impatiens wallerana,* and named 'Salmon Sunrise' is provided. This new cultivar was the result of a controlled breeding program wherein a plant designated 434-2 (non-patented in the United States) was pollinated by a plant designated 394-3 (non-patented in the United States). The new cultivar is early blooming and forms in abundance attractive fully double salmon blooms. The foliage is medium green. The plant exhibits a good basal-branching character and exhibits an upright mounded growth habit. The new cultivar can be readily distinguished from the 'Rosebud Salmon' cultivar (non-patented in the United States) in view of its propensity for earlier blooming, smaller flowers, and larger leaves.

1 Drawing Sheet

SUMMARY OF THE INVENTION

The present invention provides a new and distinctive Impatiens plant, botanically known as *Impatiens wallerana,* and hereinafter referred to by the cultivar name 'Salmon Sunrise'.

The new cultivar is the product of a planned breeding program. More specifically, the breeding program which resulted in the production of the new cultivar was carried out in a controlled environment during Sep., 1991, at Elburn, Ill., U.S.A. The female parent (i.e., the seed parent) was a plant designated 434-2 (non-patented in the United States) which exhibits salmon-orange single flowers and medium green foliage. The male parent (i.e., the pollen parent) was a plant designated 394-3 (non-patented in the United States) which exhibits light scarlet double flowers with medium green foliage. The parentage of the new cultivar can be summarized as follows:

434-2×394-3.

The seeds resulting from the above pollination were sown and plantlets were obtained which were physically and biologically different from each other. Selective study resulted in the identification of a single plant of the new cultivar. This plant had distinctive fully double salmon blooms and initially was designated 752-2.

It was found that the new cultivar of the present invention:

(a) exhibits attractive fully double salmon blooms in abundance,
(b) is early blooming,
(c) forms medium green foliage,
(d) exhibits a good basal-branching character, and
(e) exhibits an upright mounded growth habit.

Asexual reproduction of the new cultivar by stem cuttings taken during May and September, 1993, and during October, 1994, at Elburn, Ill., U.S.A., has demonstrated that the characteristics of the new cultivar as herein described are firmly fixed and are retained through successive generations of such asexual propagation.

The 'Salmon Sunrise' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Rosebud Salmon' cultivar (non-patented in the United States), it is found that the new variety is at least two weeks earlier to bloom, has smaller flowers (e.g., approximately 3.5 to 4.0 cm. in diameter vs. approximately 4.0 to 5.0 cm.), and larger leaves (e.g., approximately 5.8 to 6.2 cm.×approximately 3.2 to 4.1 cm. vs. approximately 3.5 to 4.5 cm.×approximately 2.5 to 3.5 cm.).

When plant material of the 'Salmon Sunrise' cultivar is subjected to standard random amplified polymorphic DNA marker analysis (RAPD) using polymerase chain reaction (PCR) and a known unique set of DNA primers, it is found to exhibit a different fingerprint map when compared to that of 'Rosebud Salmon' cultivar which confirms its genetic distinctiveness.

Plants of the new cultivar will be marketed under the FIESTA trademark by Geo. J. Ball, Inc.

BRIEF DESCRIPTION OF THE PHOTOGRAPHS

The accompanying photographs show the new 'Salmon Sunrise' cultivar with colors being as nearly true as it is reasonably possible to make the same in color illustrations of this character. The plants were being grown in greenhouses at West Chicago, Ill., U.S.A.

FIG. 1 illustrates the general appearance of an overall plant as seen primarily from above.

DETAILED DESCRIPTION

Figure 2:
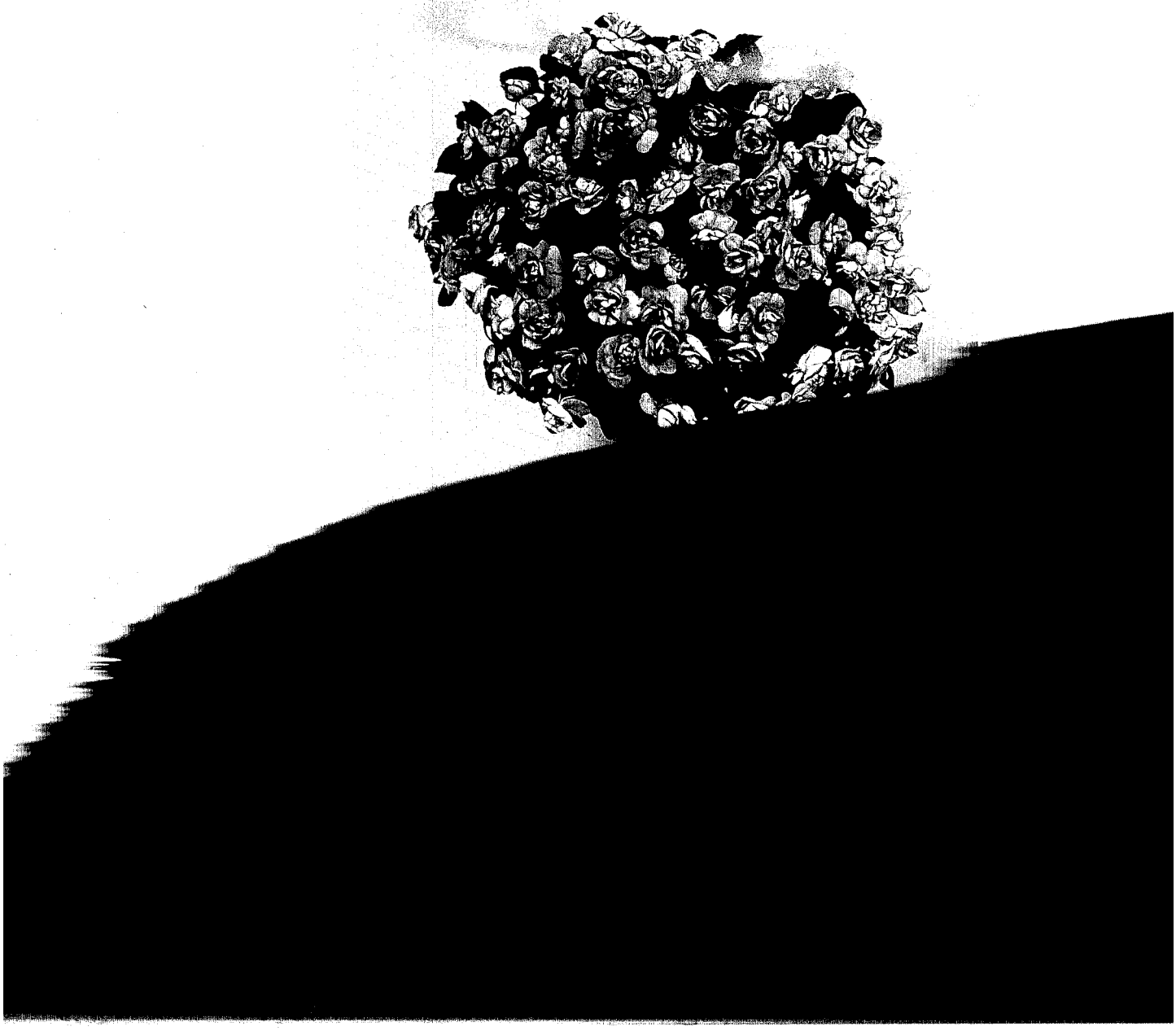
FIG. 2 illustrates the general appearance of a typical floret.

The chart used in the identification of colors described herein is The R.H.S. Colour Chart of The Royal Horticultural Society, London, England. The color values were determined on Jan. 18, 1995. The readings were taken between 10:00 and 11:00 a.m. under 2,000 footcandles of light at West Chicago, Ill., U.S.A. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type cutting.*—Two or three vegetative node stem cuttings from near the centers of the plants.

*Time to initiate roots.*—Approximately 7 to 14 days with the shorter times generally being experienced in the summer and the longer times in the winter.

*Rooting habit.*—Fibrous, and branching.

Plant description:

*Habit of growth.*—Basal-branching, and exhibits a medium upright mounded growth habit.

*Form.*—A mature plant at 8 weeks after the planting of a rooted cutting commonly measures approximately 18.0 to 19.0 cm. in height and approximately 22.0 to 25.0 cm. in width compared to approximately 17.0 to 19.0 cm. in height and approximately 19.0 to 21.0 cm. in width for the 'Rosebud Salmon' cultivar.

*Foliage.*—The configuration is ovate with an acuminate tip. The leaves of the new cultivar commonly measure approximately 5.8 to 6.2 cm. in length and approximately 3.2 to 4.1 cm. in width while those of the 'Rosebud Salmon' cultivar commonly measure approximately 3.5 to 4.5 cm. in length approximately 2.5 to 3.5 cm. in width. The foliage of the new cultivar is Green Group 137A (adaxial) and Green Group 137D (abaxial). This can be compared to Green Group 137B (adaxial) and Green Group 138C (abaxial) for the 'Rosebud Salmon' cultivar. The stem color is Green Group 143B with streaks of Greyed-Purple Group 185A for both the 'Salmon Sunrise' and the 'Rosebud Salmon' cultivars.

Flower description:

*Flowering habit.*—Freely flowering. Small round buds become more oval with maturity and flowers open in a rose-like fashion.

*Natural flowering season.*—Early blooming and blooms throughout the year in a greenhouse environment.

*Flowers borne.*—Slightly above the foliage.

*Flower color.*—Red Group 52C on fully opened petals with the central area of tightly packed petals commonly being Red Group 52B (adaxial) and slightly paler than Red Group 52D (abaxial). This can be compared to Red Group 51C (adaxial) and Red Group 51D (abaxial) for the 'Rosebud Salmon' cultivar.

*Quantity of flowers.*—Very floriferous. A mature plant commonly is totally covered with blooms.

*Number of petals.*—Fully double and petals commonly are too numerous to readily count.

*Petal shape.*—Round to oblong.

*Flower size.*—Approximately 3.5 to 4.0 cm. in diameter. This can be compared to a diameter of 4.0 to 5.0 cm. for the 'Rosebud Salmon' cultivar.

*Spur.*—Approximately 2.8 to 3.0 cm. in length and slightly curved.

*Spur color.*—Yellow-Green Group 145C.

*Reproductive organs.*—The stamens are multiple in number and the styles and ovaries are generally typical of the species and non-distinctive.

I claim:

1. A new and distinct cultivar of *Impatiens wallerana* plant named 'Salmon Sunrise' substantially as herein shown and described, which:

(a) exhibits attractive fully double salmon blooms in abundance,
(b) is early blooming,
(c) forms medium green foliage,
(d) exhibits a good basal-branching character, and
(e) exhibits an upright mounded growth habit.

* * * * *